United States Patent [19]
Ueda et al.

[11] Patent Number: 4,764,514
[45] Date of Patent: Aug. 16, 1988

[54] OXOTHIAZOLIDINE COMPOUND AND COMPOSITION CONTAINING SAME

[75] Inventors: Ikuo Ueda, Uenohigashi; Yousuke Katsura, Uenonishi, both of Japan

[73] Assignee: Fujisawa Pharmaceutical Co., Ltd., Osaka, Japan

[21] Appl. No.: 855,904

[22] Filed: Apr. 24, 1986

[30] Foreign Application Priority Data

May 14, 1985 [GB] United Kingdom ............... 8512163

[51] Int. Cl.$^4$ ............... A61K 31/495; C07D 277/14; C07D 417/06; C07D 417/12
[52] U.S. Cl. ............... 514/252; 514/212; 514/218; 514/326; 514/342; 514/369; 540/575; 540/603; 544/133; 544/369; 546/209; 546/280; 546/284; 548/187; 548/188
[58] Field of Search ............... 540/575, 603; 544/133, 544/369; 546/209, 280, 284; 548/188, 187; 514/212, 218, 234, 252, 326, 342, 369

[56] References Cited

U.S. PATENT DOCUMENTS 3,309,377  3/1967  Surrey ............... 548/186

FOREIGN PATENT DOCUMENTS 2098215  11/1982  United Kingdom .

OTHER PUBLICATIONS

Arimura, CA 87-84979h.

*Primary Examiner*—Donald G. Daus
*Assistant Examiner*—Cecilia Shen
*Attorney, Agent, or Firm*—Jordan B. Bierman

[57] ABSTRACT

This invention provides a oxothiazolidine compound of the formula:

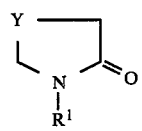

wherein
$R^1$ is acyl;
di(lower)alkylamino(lower)alkylcarbamoyl(lower)alkyl; arylcarbamoyl(lower)alkyl; ar(lower)alkylcarbamoyl(lower)alkyl; heterocyclic carbamoyl(lower)alkyl; heterocyclic(lower)alkylcarbamoyl(lower)alkyl; thiazolidinylcarbonyl(lower)alkyl; morpholinylcarbonyl(lower)alkyl or a group of the formula:

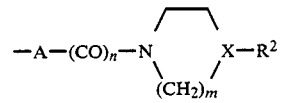

in which
A is lower alkylene;
n is an integer of 0 or 1;
m is an integer of 2 or 3;
X is —N—,

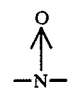

or —CH— and
$R^2$ is hydroxy;
lower alkyl which may have hydroxy;
ar(lower)alkyl which may have halogen;
arylthio which may have halogen;
acyl or heterocyclic group and
Y is —S—,

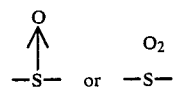

or pharmaceutically acceptable salt thereof.

This compound is useful as cognition activator. This invention further provides processes for the preparation of this compound and pharmaceutical composition comprising compound of the above formula.

9 Claims, No Drawings

OXOTHIAZOLIDINE COMPOUND AND COMPOSITION CONTAINING SAME

This invention relates to a new oxothiazolidine compound. More particularly, it relates to a new oxothiazolidine compound and pharmaceutically acceptable salt thereof which are useful as a pharmacological agent, especially cognition activator, to processes for the preparation thereof and to a pharmaceutical composition comprising the same.

The oxothiazolidine compound of this invention can be represented by the formula:

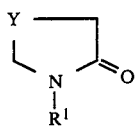
(I)

wherein
R¹ is acyl,
  di(lower)alkylamino(lower)alkylcarbamoyl(lower)alkyl,
  arylcarbamoyl(lower)alkyl,
  ar(lower)alkylcarbamoyl(lower)alkyl,
  heterocyclic carbamoyl(lower)alkyl,
  heterocyclic(lower)alkylcarbamoyl(lower)alkyl
    thiazolidinylcarbonyl-(lower)alkyl,
  morpholinylcarbonyl-(lower)alkyl or a group of the formula:

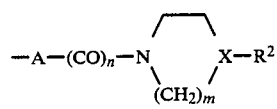

in which
A is lower alkylene,
n is an integer of 0 or 1,
m is an integer of 2 or 3,
X is —N—,

or —CH— and
R² is hydroxy,
  lower alkyl which may have hydroxy,
  ar(lower)alkyl which may have halogen,
  arylthio which may have halogen,
  aryl or heterocyclic group and
Y is —S—,

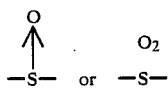

or pharmaceutically acceptable salt thereof.

The pharmaceutically acceptable salt of the compound (I) may include an acid addition salt such as fumarate, maleate, acetate, citrate, hydriodate, hydrochloride, sulfate, phosphate, benzoate and the like.

The compound (I) and salt thereof can be prepared, for example, by the following processes.

(1) Process 1:

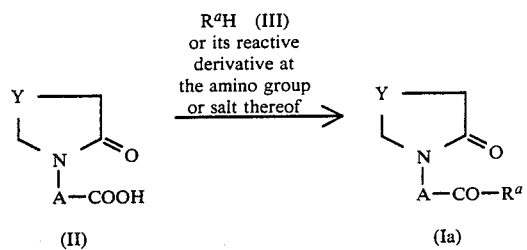

(2) Process 2:

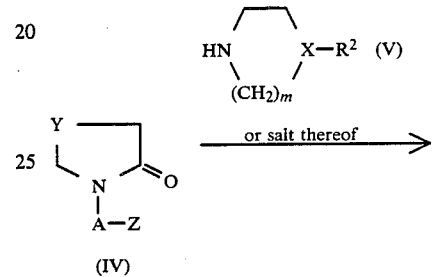

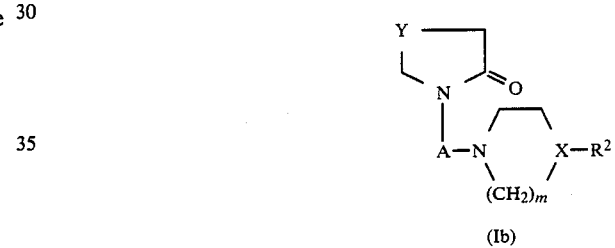

(3) Process 3:

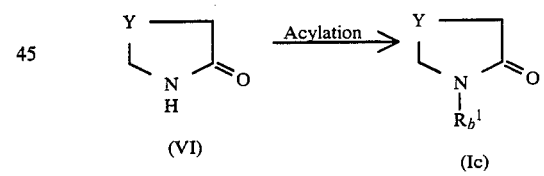

(4) Process 4:

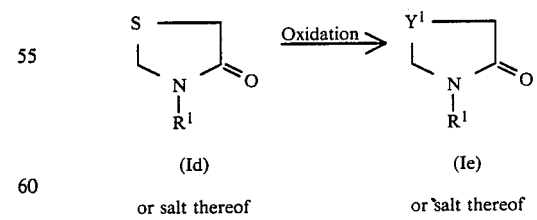

wherein
R², A, m, X and Y are each as defined above,
Rᵃ is di(lower)alkylamino(lower)alkylamino,
  arylamino,
  ar(lower)alkylamino,
  heterocyclic amino, heterocyclic(lower)alkylamino,
thiazolidinyl,
morpholinyl, or
a group of the formula:

$$-N\begin{pmatrix} \phantom{X} \\ (CH_2)_m \end{pmatrix} X-R^2$$

in which $R^2$, X and m are each as defined above,
$R_b^1$ is acyl, $$-\overset{\overset{O}{\uparrow}}{S}- \quad \text{or} \quad -\overset{O_2}{S}-$$

and
Z is acid residue.

The starting compounds (II) and (IV) are novel ones and can be prepared, for example, by the following preparations.

<chemical scheme>

(VI) or salt thereof $Z^b$—A—Z (IX) (Preparation 3)    $Z^a$—A—V (VII) (Preparation 1)

(IV)    (VIII)

Removal of carboxy-protective group (Preparation 2)

(II) or salt thereof
</chemical scheme> wherein
A and Z are each as defined above,
V is a protected carboxy and
$Z^a$ and $Z^b$ are each acid residue.

The compound (VI) is a known compound, preparation thereof is described in Yakugaku Zasshi, 76, 73 (1955).

The salt of the compounds (II) and (VI) may include a salt with an inorganic or organic base such as alkali metal hydride (e.g. lithium hydride, etc.), alkyl alkali metal (e.g. butyl lithium, etc.), alkali metal (e.g. sodium, potassium, etc.), alkali metal hydroxide (e.g. sodium hydroxide, potassium hydroxide, etc.), trimethylamine, N,N-dicyclohexylamine and the like.

The salt of the compounds (Ia), (Ib), (Id), (Ie), (III) and (V) may include inorganic or organic acid addition salts as those exemplified in the explanation of pharmaceutically acceptable salt of the compound (I).

In the above and subsequent description of this specification, suitable examples and illustrations of the various definitions are explained in detail in the followings.

The term "lower" is intended to mean 1 to 6 carbon atom(s).

The term "acyl" may include a residue of organic acid such as organic carboxylic acid, organic sulfonic acid, organic carbamic acid, organic carbonic acid and the like.

Suitable "acyl" may include aroyl (e.g. benzoyl, naphthoyl, etc.) which may have one or more suitable substituent(s) such as lower alkoxy (e.g. methoxy, ethoxy, propoxy, etc.), halogen (e.g. fluorine, chlorine, bromine, iodine), lower alkyl (e.g. methyl, ethyl, etc.) and trihalomethyl (e.g. trifluoromethyl, etc.); arenesulfonyl (e.g. benzenesulfonyl, toluenesulfonyl, etc.) which may have one or more suitable substituent(s) such as lower alkoxy (e.g. methoxy, ethoxy, propoxy, etc.) and halogen (e.g. fluorine, chlorine, bromine, iodine); heterocyclic carbonyl (e.g. pyridylcarbonyl, furoyl, thenoyl, etc.) and the like.

Suitable "lower alkyl" in the term "di(lower)alkylamino(lower)alkylcarbamoyl(lower)alkyl", "arylcarbamoyl(lower)alkyl", "ar(lower)alkylcarbamoyl(lower)alkyl", "heterocyclic carbamoyl(lower)alkyl", "heterocyclic(lower)alkylcarbamoyl(lower)alkyl", "thiazolidinylcarbonyl-(lower)alkyl", "morpholinylcarbonyl-(lower)alkyl", "lower alkyl" and "di(lower)alkylamino(lower)alkylamino" may include methyl, ethyl, propyl, isopropyl, butyl, isobutyl, sec-butyl, t-butyl, pentyl, hexyl and the like.

Suitable "aryl" in the terms "arylcarbamoyl(lower)alkyl", "arylthio" and "arylamino" may include phenyl, tolyl, xylyl, naphthyl and the like.

Suitable "ar(lower)alkyl" in the terms "ar(lower)alkylcarbamoyl(lower)alkyl", "ar(lower)alkyl" and "ar(lower)alkylamino" may include mono(or di or tri)phenyl(lower)alkyl such as benzyl, diphenylmethyl, trityl, phenethyl and the like.

Suitable "heterocyclic" group in the terms "heterocyclic carbamoyl(lower)alkyl", "heterocyclic(lower)alkylcarbamoyl(lower)alkyl", "heterocyclic group", "heterocyclic amino" and "heterocyclic(lower)alkylamino" may include saturated or unsaturated, monocyclic or polycyclic heterocyclic group containing at least one hetero-atom such as an oxygen, sulfur, nitrogen atom and preferred "heterocyclic group" may be 5 or 6-membered heteromonocyclic group containing oxygen or nitrogen atom such as furyl, pyridyl and the like, and benzene-fused heterocyclic group containing nitrogen atom such as indolyl and the like.

Suitable "lower alkylene" may include methylene, methylmethylene, ethylene, trimethylene, propylene, ethylethylene, tetramethylene, pentamethylene, hexamethylene and the like.

"Halogen" may include fluorine, chlorine, bromine and iodine.

Suitable "acid residue" may include halogen (fluorine, chlorine, bromine and iodine), arenesulfonyl and the like.

Suitable "Protected carboxy" may include esterified carboxy such as lower alkoxycarbonyl (e.g. methoxy-carbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl) and the like.

Preferable embodiments of the object compound (I) are as follows.

"Preferable embodiments of $R^1$ is acyl [more preferably aroyl which may have one or more suitable substituent(s)] [most preferably benzoyl which may have one or two substituent(s) selected from lower alkoxy, halogen, lower alkyl and trihalomethyl], arenesulfonyl which may have one or more suitable substituent(s) [most preferably benzenesulfonyl which may have lower alkoxy] and heterocyclic carbonyl [[most preferably pyridylcarbonyl, furoyl and thenoyl]], di(lower)alkylamino(lower)alkylcarbamoyl(lower)alkyl, arylcarbamoyl(lower)alkyl [more preferably phenylcarbamoyl(lower)alkyl and xylylcarbamoyl(lower)alkyl], ar(lower)alkylcarbamoyl(lower)alkyl [more preferably phenyl(lower)alkylcarbamoyl(lower)alkyl], heterocyclic carbamoyl(lower)alkyl [more preferably pyridylcarbamoyl(lower)alkyl], heterocyclic(lower)alkylcarbamoyl(lower)alkyl [more preferably furyl(lower)alkylcarbamoyl(lower)alkyl], thiazolidinylcarbonyl(lower)alkyl, morpholinylcarbonyl(lower)alkyl or a group of the formula:

$$-A-(CO)_n-N\diagup\diagdown X-R^2$$
$$\diagdown(CH_2)_m\diagup$$

in which
A is lower alkylene,
n is an integer of 0 or 1,
m is an integer of 2 or 3,
X is —N—, $$\overset{O}{\underset{-N-}{\uparrow}}$$

or —CH— and
$R^2$ is hydroxy,
  lower alkyl which may have hydroxy,
  ar(lower)alkyl which may have halogen [more preferably mono(or di)phenyl(lower)alkyl which may have halogen],
  arylthio which may have halogen [more preferably phenylthio which may have halogen],
  acyl [more preferably aroyl [most preferably benzoyl] and arenesulfonyl which may have halogen [most preferably benzenesulfonyl which may have halogen]] or heterocyclic group [more preferably indolyl] and;
Y is —S—, $$\overset{O}{\underset{-S-}{\uparrow}}\quad\text{or}\quad\overset{O_2}{\underset{-S-}{\uparrow}}$$

The processes and preparation as illustrated above are explained in more detail in the followings.

Process 1:
The object compound (Ia) or salt thereof can be prepared by reacting the compound (II) or its reactive derivative at the carboxy group or salt thereof with the compound (III) or its reactive derivative at the amino group or salt thereof.

The reactive derivative at the carboxy of the compound (II) may include acid halide (e.g. acid chloride, acid bromide, etc.), acid anhydride, acid azide, activated amide or activated ester (e.g. succinimide ester, etc.), and the like.

The reactive derivative at the amino group of the compound (III) may include a silyl derivative formed by the reaction of the compound (III) with a silyl compound (e.g. bis(trimethylsilyl)acetamide, trimethylsilylacetamide, etc.) and the like.

When the starting compound (II) is used in a free acid form, the reaction may preferably be conducted in the presence of a conventional condensing agent (e.g. dicyclohexylcarbodiimide, etc.).

The reaction is usually conducted without a solvent or in a solvent which does not adversely influence the reaction such as N,N-dimethylformamide, dimethylsulfoxide, tetrahydrofuran, dichloromethane, chloroform, toluene, xylene, pyridine or a mixture thereof.

The reaction can also be conducted in the presence of an organic or inorganic base such as alkali metal (e.g. sodium), alkaline earth metal (e.g. calcium), alkali or alkaline earth metal hydride (e.g. sodium hydride, calcium hydride, etc.), alkali or alkaline earth metal hydroxide (e.g. sodium hydroxide, potassium hydroxide, calcium hydroxide, etc.), alkali or alkaline earth metal carbonate or bicarbonate (e.g. sodium carbonate, potassium carbonate, sodium bicarbonate), alkali or alkaline earth metal alkoxide (e.g. sodium ethoxide, lithium methoxide, magnesium methoxide), trialkylamine (e.g. triethylamine), pyridine, bicyclodiaza compound (e.g. 1,5-diazabicyclo[3,4,0]nonene-5, 1,5-diazabicyclo[5,4,0]undecene-5, etc.) and the like.

The reaction temperature is not critical and this reaction can be conducted within the temperature range of cooling to heating.

Process 2:
The compound (Ib) or salt thereof can be prepared by reacting the compound (IV) with the compound (V) or salt thereof.

The reaction is usually carried out in a solvent which does not adversely influence the reaction such as N,N-dimethylformamide, dimethylsulfoxide, tetrahydrofuran, chloroform and the like.

The reaction temperature is not critical and this reaction can be conducted within the temperature range of cooling to heating.

Process 3:
The compound (Ic) can be prepared by reacting the compound (VI) or salt thereof with an acylating agent.

The acylating agent to be used in this reaction includes an organic acid (i.e. $R_b^1$OH (X), in which $R_b^1$ is acyl) and its reactive derivative.

The suitable reactive derivative of the compound (X) may be a conventional one such as an acid halide (e.g. acid chloride, acid bromide, etc.), an acid azide an acid anhydride, an activated amide, an activated ester, an isocyanate and the like.

When free acid is used as an acylating agent, the acylation reaction may preferably be conducted in the presence of a conventional condensing agent.

The reaction is usually conducted in a solvent which does not adversely influence the reaction such as N,N-dimethylformamide, dimethylsulfoxide, tetrahydrofuran, dichloromethane, chloroform, pyridine or a mixture thereof.

The reaction can also be conducted in the presence of an organic or inorganic base as those exemplified in the explanation of the process 1.

The reaction temperature is not critical and this reaction can be conducted within the temperature range of cooling to heating.

Process 4:

The compound (Ie) or salt thereof can be prepared by oxidizing the compound (Id) or salt thereof.

The oxidation is usually carried out by using an oxidizing agent employed for oxidizing an sulfur atom in heterocyclic ring (e.g. m-chloroperbenzoic acid, hydrogen peroxide, potassium permanganate, etc).

The reaction is usually conducted in a solvent which does not adversely influence the reaction such as N,N-dimethylformamide, dimethylsulfoxide, tetrahydrofuran, dichloromethane, chloroform, pyridine or a mixture thereof.

The reaction temperature is not critical and the reaction can be carried out under cooling to warming.

Preparation 1:

The compound (VIII) can be prepared by reacting the compound (VI) or salt thereof with the compound (VII).

The reaction condition of this reaction is substantially the same as those of the process 2 mentioned above.

Preparation 2:

The compound (II) or salt thereof can be prepared by subjecting the compound (VIII) to removal reaction of the carboxy-protective group.

The removal reaction of this process may include a conventional reaction for removing carboxy-protective group such as hydrolysis and the like.

The hydrolysis is preferably carried out in the presence of inorganic or organic acid (e.g. hydrochloric acid, sulfuric acid, acetic acid, trifluoroacetic acid, etc.), or inorganic or organic base (e.g. sodium hydroxide, etc.).

The reaction is usually carried out in a solvent which does not adversely influence the reaction such as water, methanol, ethanol, propanol, acetic acid and the like, at a temperature range of cooling to heating.

Preparation 3:

The compound (IV) can be prepared by reacting the compound (VI) or salt thereof with the compound (IX).

The reaction condition of this reaction is substantially the same as those exemplified in the process 2.

The object compounds in the above processes and preparations can be purified and isolated from the reaction mixture, and converted to the desired salts in a conventional manner.

The object compound (I) of this invention and pharmaceutically acceptable salt thereof are useful as pharmacological agents. More specifically, they are cognition activators which are potentially useful in treating patients suffering from senility, lost or impaired memory or amnesia. In addition, the object compound (I) may be useful in treating patients having certain learning disabilities.

The following test is given for the purpose of illustrating pharmacological activity of the compound (I) of this invention.

Test 1 [Effect of the compound (I) on electroconvulsive shock-induced amnesia]

Animals:

Male ddY mice aged 6 weeks and weighing 30-35 g were used in groups of 20.

Apparatus:

The step-through passive avoidance equipment consisted of two V-shaped compartment of same size (light and dark) which was divided by a guillotine door. The chamber size was as follows, lower diameter: 4 cm, upper diameter: 10 cm, height: 10 cm, length: 14 cm. The light chamber was constructed entirely of clear plastic. It was illuminated by a 60 W light positioned about 10 cm above the chamber. The dark chamber was constructed of black-colored plastic. The each floor consisted of 24 stainless steel bars which were 2 mm in diameter and 5 mm apart. A foot shock of constant voltage AC pulse could be delivered to the bars by shock generator (Ohara-Ika Sangyo).

Procedure:

Training procesure was to place the animal in the light chamber. The animal was tamed for 30 sec, and the guillotine door was opened. When the animal had all four paws on the grid floor of the dark chamber, the guillotine door was shut, and then, foot shock of 60 V was applied for 3 sec. The door was opened again, and the animal returned to the light chamber was removed. Immediately after acquisition of passive avoidance response, electroconvulsive shock of 22 mA 0.3 sec was given through the ears, and subsequently followed by an oral dose of test compound. Test compound was suspended in 0.5% methylcellulose solution and was also given 1 hr before the test. The animal was tested 24 hr later using the same procedure except that no shock was delivered. The animal's latency to step through the dark chamber was measured.

If the animal did not step through into the dark chamber within 300 sec, the trial was termed.

Test compound:

| Test Compound No. | Formula |
|---|---|
| 1 | (structure) |
| 2 | (structure) |

Test result:

Effect of drugs on electroconvulsive shock-induced amnesia is shown in Table 1.

Electroconvulsive shock after passive avoidance training produced complete amnesia. On the other hand, the administration of test compounds significantly prevented the electroconvulsive shock-induced disruption of the memory of a passive avoidance response in mice, that is, reduced retention time was reversed (increased) by the administration of these drugs.

TABLE 1

Effect of drugs on electroconvulsive shock-induced amnesia.

| Treatment | Retention time (sec) |
| --- | --- |
| None | 295.8 ± 3.0** |
| ES | 76.4 ± 22.6 |
| ES + Test compound 1 (Dosage : 10 mg/kg) | 150.2 ± 5.4* |
| None | 271.0 ± 3.7** |
| ES | 72.0 ± 7.3 |
| ES + Test compound 2 (Dosage : 10 mg/kg) | 177.1 ± 3.1** |

Figures show mean ± s.e.
ES : Electroconvulsive shock
* : $p < 0.05$,
** : $p < 0.01$, Significantly different from ES.

The object compound (I) or its pharmaceutically acceptable salt can usually be administered to mammals including human beings in the form of a conventional pharmaceutical composition such as capsule, microcapsule, tablet, granule, powder, troche, syrup, aerosol, inhalation, solution, injection, suspension, emulsion, suppository, ointment, or the like.

The pharmaceutical composition of this invention can contain various organic or inorganic carrier materials, which are conventionally used for pharmaceutical purpose, such as excipient (e.g. sucrose, starch, mannit, sorbit, lactose, glucose, cellulose, talc, calcium phosphate, calcium carbonate, etc.), binding agent (cellulose, methyl cellulose, hydroxypropylcellulose, polypropylpyrrolidone, gelatin, gum arabic, polyethyleneglycol, sucrose, starch, etc.), disintegrator (e.g. starch, carboxymethyl cellulose, calcium salt of carboxymethyl cellulose, hydroxypropylstarch, sodium glycole-starch, sodium bicarbonate, calcium phosphate, calcium citrate, etc.), lubricant (e.g. magnesium stearate, talc, sodium laurylsulfate, etc.), flavoring agent (e.g. citric acid, mentol, glycine, orange powders, etc.), preservative (sodium benzoate, sodium bisulfite, methylparaben, propylparaben, etc.), stabilizer (citric acid, sodium citrate, acetic acid, etc.), suspending agent (e.g. methyl cellulose, polyvinylpyrrolidone, aluminum stearate, etc.), dispersing agent, aqueous diluting agent (e.g. water), base wax (e.g. cacao butter, polyethyleneglycol, white petrolatum, etc.).

A dosage of the present active ingredient is to be varied depending on various factors such as weight and/or age of a patient and/or the kind of the diseases, and further the kind of administration route. In general, an effective dosage can be selected from a range of about 2–1000 mg/day for an oral route, about 1–250 mg/day for an intramuscular or intravenous injection.

The total daily amount mentioned above may be divisionally given to the patient at the interval of 6–12 hours per day. Preferable single dose of the present active ingredient may be, for example, about 1–300 mg per tablet or capsule, about 1–250 mg per vial or ampoule, and so on.

The starting compounds to be used in the preparation of the object compound (I) of this invention can be specifically prepared in the following Preparations.

Preparation 1

A solution of 4-oxothiazolidine (50 g) in tetrahydrofuran (900 ml) was added dropwise to a suspension of sodium hydride (60% dispersion in mineral oil) (22.6 g) in tetrahydrofuran (850 ml) at room temperature and the mixture was allowed to warm up to reflux temperature. After the mixture was refluxed for an additional 30 minutes, ethyl bromoacetate (60 ml) was added dropwise under that condition. The mixture was refluxed further 1 hour and then cooled. Insoluble materials were removed by filtration. The filtrate was evaporated in vacuo and the residue was purified by silica gel column chromatography by eluting with chloroform to give ethyl 4-oxo-3-thiazolidinylacetate (78.5 g) as light brown powder.

mp: 35° to 39° C.

IR (Nujol): 1700, 1635 cm$^{-1}$.

NMR (CDCl$_3$, δ): 1.28 (3H, t, J=7.5 Hz), 3.58 (2H, t, J=1.0 Hz), 4.12 (2H, s), 4.22 (2H, q, J=7.5 Hz) and 4.48 (2H, q, J=1.0 Hz).

Preparation 2

The following compounds were prepared in a similar manner to that of Preparation 1.

(1) Ethyl 3-(4-oxo-3-thiazolidinyl)propionate, as colorless oil.

IR (Nujol): 1720, 1660 cm$^{-1}$.

NMR (CDCl$_3$, δ): 1.28 (3H, t, J=7 Hz), 2.62 (2H, t, J=7 Hz), 3.57 (2H, t, J=1 Hz), 3.67 (2H, t, J=7 Hz), 4.18 (2H, q, J=7 Hz), and 4.48 (2H, t, J=1 Hz).

(2) Ethyl 2-(4-oxo-3-thiazolidinyl)propionate, as colorless oil.

IR (Film): 1725, 1670 cm$^{-1}$.

NMR (CDCl$_3$, δ): 1.28 (3H, t, J=7.5 Hz), 1.49 (3H, d, J=7.5 Hz), 3.57 (2H, t, J=1.0 Hz), 4.19 (2H, q, J=7.5 Hz), 4.39 (1H, d, J=11.0 Hz), 4.51 (1H, d, J=11.0 Hz) and 4.89 (1H, q,, J=7.5 Hz).

Preparation 3

A solution of ethyl 2-(4-oxo-3-thiazolidinyl)propionate (2.60 g) in a mixture of 1N aqueous sodium hydroxide (12.8 ml) and methanol (64 ml) was stirred for 2 hours at room temperature. After the solvent was evaporated in vacuo, 1N hydrochloric acid (19.2 ml) was added to the residue and the mixture was stirred for several minutes. After the mixture was concentrated to dryness, the residue was mixed with tetrahydrofuran (50 ml) and the resultant insoluble solid was removed by filtration.

The filtrate was evaporated in vacuo to give 2-(4-oxo-3-thiazolidinyl)propionic acid (2.25 g) as light yellow semi-solid.

IR (Nujol): 1715, 1610–1680 cm$^{-1}$.

NMR (CDCl$_3$, δ): 1.52 (3H, d, J=7.5 Hz), 3.65 (2H, s), 4.44 (1H, d, J=11.0 Hz), 4.56 (1H, d, J=11.0 Hz), 4.93 (1H, q, J=7.5 Hz) and 9.85 (1H, s).

Preparation 4

A solution of 4-oxothiazolidine (3.00 g) in tetrahydrofuran (40 ml) was added dropwise to a suspension of sodium hydride (60% dispersion in mineral oil) (1.28 g) in tetrahydrofuran (30 ml) at room temperature with stirring. 3-Bromo-1-chloropropane (3.15 ml) was added dropwise to the mixture under refluxing and the mixture was allowed to reflux for 9 hours. After the resultant precipitate was removed by filtration, the filtrate was evaporated in vacuo. The residue was chromatographed on basic alumina by eluting with ethyl acetate and then with a 10:1 mixture of toluene and ethyl acetate to give 3-(3-chloropropyl)-4-oxothiazolidine (2.60 g) as colorless oil.

IR (Film): 1760, 1650 cm$^{-1}$.

NMR (CDCl$_3$, δ): 2.07 (2H, quint, J=7 Hz), 3.55 (2H, t, J=7 Hz), 3.57 (2H, t, J=7 Hz), 3.58 (2H, s), and 4.43 (2H, t, J=1 Hz).

Preparation 5

The following compound was prepared in a similar manner to that of Preparation 3.

4-Oxo-3-thiazolidinylacetic acid mp: 176° to 178° C. (unrecrystallized).

IR (Nujol): 1880, 1735 (shoulder), 1705, 1690 cm$^{-1}$.

NMR (DMSO-d$_6$, δ): 3.53 (2H, t, J=1.5 Hz), 4.03 (2H, s) and 4.43 (2H, t, J=1.5 Hz).

Preparation 6

Thionyl chloride (2.00 ml) was added dropwise to a solution of 4-oxo-3-thiazolidinylacetic acid (1.60 g) in a mixture of dichloromethane (20 ml) and tetrahydrofuran (5.0 ml) at room temperature. After the mixture was stirred for 5 hours at the same temperature, the solvent was evaporated in vacuo to give 4-oxo-3-thiazolidinylacetyl chloride (1.78 g) as brown semisolid.

IR (Nujol): 1770, 1710, 1650 cm$^{-1}$.

The following Examples are given for the purpose of illustrating this invention.

EXAMPLE 1

A mixture of ethyl 4-oxo-3-thiazolidinylacetate (25.0) and 1-diphenylmethylpiperazine (67.0 g) was held at 135° C. for 15 hours. The reaction mixture was chromatographed on basic alumina by eluting with a 20:1 mixture of toluene and ethyl acetate to give light brown powder (46.4 g), which was recrystallized from a mixture of ethanol and n-hexane to afford 1-(4-oxo-3-thiazolidinyl)acetyl-4-diphenylmethylpiperazine (30.7 g) as slightly brown prisms.

mp: 147° to 148° C.

IR (Nujol): 1670 (shoulder), 1660 cm$^{-1}$.

NMR (DMSO-d$_6$, δ): 2.10–2.38 (4H, m), 3.37–3.63 (6H, m), 4.13 (2H, s), 4.32 (1H, s), 4.37 (2H, s), and 7.07–7.52 (10H, m).

EXAMPLE 2

The following compounds were prepared in a similar manner to that of Example 1.

(1) 1-(4-Oxo-3-thiazolidinyl)acetyl-4-benzylpiperazine, as slightly brown prisms.

mp: 136° to 137° C. (recrystallized from a mixture of ethyl acetate and n-hexane).

IR (Nujol): 1685, 1665, 1645 cm$^{-1}$.

NMR (CDCl$_3$, δ): 2.36–2.53 (4H, m), 3.40–3.70 (4H, m), 3.53 (2H, s), 3.58 (2H, t, J=1 Hz), 4.18 (2H, s), 4.52 (2H, t, J=1 Hz), and 7.32 (5H, s).

(2) 1-(4-Oxo-3-thiazolidinyl)acetyl-4-isopropylpiperazine, as slightly brown prisms.

mp: 126° to 128° C. (recrystallized from a mixture of ethyl acetate and n-hexane).

IR (Nujol): 1675, 1650 cm$^{-1}$.

NMR (CDCl$_3$, δ): 1.04 (6H, d, J=6.5 Hz), 2.50 (4H, t, J=5.0 Hz), 2.59 (1H, m, J=6.5 Hz), 3.52 (4H, t, J=5.0 Hz), 3.57 (2H, t, J=1.0 Hz), 4.18 (2H, s) and 4.52 (2H, t, J=1.0 Hz).

(3) Monomaleic acid salt of 1-(4-oxo-3-thiazolidinyl)acetyl-4-methylpiperazine, as light brown crystals.

mp: 146° to 148° C. (recrystallized from ethanol).

IR (Nujol): 1660, 1650 cm$^{-1}$.

NMR (DMSO-d$_6$, δ): 2.82 (3H, s), 3.05–3.32 (4H, m), 3.53 (2H, t, J=1 Hz), 3.60–3.78 (4H, m), 4.28 (2H, s), 4.38 (2H, t, J=1 Hz), 6.10 (2H, s) and 12.00 (2H, br s).

(4) 1-[3-(4-Oxo-3-thiazolidinyl)propionyl]-4-diphenylmethylpiperazine, as slightly yellowish-brown prisms.

mp: 184° to 185° C. (recrystallized from a mixture of ethanol and ethyl acetate).

IR (Nujol): 1665, 1635 cm$^{-1}$.

NMR (CDCl$_3$, δ): 2.28–2.45 (4H, m), 2.58 (3H, t, J=6 Hz), 3.35–3.72 (8H, m), 4.25 (1H, s), 4.48 (2H, t, J=1 Hz) and 7.08–7.48 (10H, m).

(5) 1-[2-(4-Oxo-3-thiazolidinyl)propionyl]-4-diphenylmethylpiperazine, as slightly brown prisms.

mp: 151° to 152° C. (recrystallized from a mixture of ethyl acetate and n-hexane).

IR (Nujol): 1670, 1640 cm$^{-1}$.

NMR (CDCl$_3$, δ): 1.33 (3H, d, J=7 Hz), 2.40–2.48 (4H, m), 3.37–3.68 (6H, m), 4.20 (1H, s), 4.40 (2H, t, J=1 Hz), 5.11 (1H, q, J=7 Hz) and 7.08–7.48 (10H, m).

(6) 1-(4-Oxo-3-thiazolidinyl)acetyl-4-hydroxypiperidine, as colorless prisms.

mp: 153° to 155° C. (recrystallized from ethanol).

IR (Nujol): 3380, 3320, 1670, 1635, 1610 cm$^{-1}$.

NMR (DMSO-d$_6$, δ): 1.03–2.00 (4H, m), 2.75–4.00 (5H, m), 3.50 (2H, t, J=1 Hz), 4.17 (2H, s), 4.38 (2H, t, J=1 Hz) and 4.68 (1H, d, J=4 Hz).

(7) ¾ Fumaric acid salt of N-[2-(diisopropylamino)ethyl]-4-oxo-3-thiazolidinylacetamide, as slightly brown prisms.

mp: 152° to 154° C. (recrystallized from a mixture of ethanol and n-hexane).

IR (Nujol): 3175, 2400, 1690, 1670 cm$^{-1}$.

NMR (DMSO-d$_6$, δ): 1.08 (12H, d, J=6 Hz), 2.64–2.79 (2H, m), 2.96-3.38 (4H, m), 3.51 (2H, t, J=1 Hz), 3.91 (2H, s), 4.42 (2H, t, J=1 Hz), 6.49 (3/2H, S), 8.04 (3H, br s) and 8.41 (1H, t, J=6 Hz).

EXAMPLE 3

A mixture of 2-(4-oxo-3-thiazolidinyl)propionic acid (2.00 g), 2.6-dimethylaniline (1.38 g), and dicyclohexylcarbodiimide (2.35 g) in chloroform (15 ml) was refluxed for 48 hours. The resultant precipitate was removed by filtration and the filtrate was evaporated in vacuo. The residue was triturated with diethyl ether and recrystallized from ethanol to give N-(2,6-dimethylphenyl)-2-(4-oxo-3-thiazolidinyl)propionamide (1.45 g) as colorless prisms.

mp: 153° to 154° C.

IR (Nujol): 3260, 1660 cm$^{-1}$.

NMR (DMSO-d$_6$, δ): 1.49 (3H, d, J=7.5 Hz), 2.12 (6H, s), 3.55 (2H, t, J=1.0 Hz), 4.53 (1H, d, J=9.0 Hz), 4.66 (1H, d, J=9.0 Hz), 4.83 (1H, q, J=7.5 Hz), 7.05 (3H, s) and 9.35 (1H, br s).

EXAMPLE 4

Triethylamine (2.13 ml) was added to a mixture of 3-(3-chloropropyl)-4-oxothiazolidine (2.50 g), 1-diphenylmethylpiperazine (3.86 g) and potassium iodide (2.54 g) in N,N-dimethylformamide (25 ml) at room temperature with stirring and the mixture was allowed to warm at 45° C. for 15 hours. After the solvent was evaporated in vacuo, the residue was mixed with water (50 ml) and extracted with dichloromethane (40 ml). The extract was washed with water, dried over magnesium sulfate and evaporated in vacuo. The residue was triturated with a mixture of ethanol and diethyl ether to give light brown powder (2.80 g), which was recrystallized from methanol to afford monohydriodic acid salt of 1-[3-(4-oxo-3-thiazolidinyl)propyl]-4-diphenylmethylpiperazine (1.80 g) as colorless prisms.

mp: 216° to 217° C.

IR (Nujol): 1665 cm$^{-1}$.

NMR (DMSO-d$_6$, δ): 1.63-2.17 (2H, m), 2.20-3.35 (12H, m), 3.52 (2H, s), 4.45 (2H, s), 4.53 (1H, s), and 7.15-7.53 (10H, m).

EXAMPLE 5

A solution of 4-methoxybenzoyl chloride (20.7 g) in tetrahydrofuran (50 ml) was added dropwise to a mixture of 4-oxo-thiazolidine (12.5 g) and triethylamine (16.9 ml) in tetrahydrofuran (200 ml) at −5° C. with stirring. The mixture was stirred at that temperature for 3 hours and at room temperature for 4 hours, and allowed to stand overnight. After the solvent was evaporated in vacuo, the residue was mixed with water and extracted with ethyl acetate. The extract was washed with saturated aqueous sodium hydrogen carbonate and then with water, dried over magnesium sulfate and evaporated in vacuo. The residue was recrystallized from a mixture of ethyl acetate and n-hexane to give 3-(4-methoxybenzoyl)-4-oxothiazolidine (18.1 g) as slightly brown prisms.

mp: 123° to 124° C.

IR (Nujol): 1730, 1650 cm$^{-1}$.

NMR (CDCl$_3$, δ): 3.63 (2H, s), 3.80 (3H, s), 4.83 (2H, s), 6.86 (2H, d, J=8.5 Hz) and 7.61 (2H, d, J=8.5 Hz).

EXAMPLE 6

The following compound was prepared in a similar manner to that of Example 5.

3-(2-Methoxybenzoyl)-4-oxothiazolidine, as slightly yellowish-brown prisms.

mp: 90° to 91° C. (recrystallized from a mixture of ethanol and n-hexane).

IR (Nujol): 1730, 1645 cm$^{-1}$.

NMR (CDCl$_3$, δ): 3.59 (2H, s), 3.75 (3H, s), 4.88 (2H, s), and 6.78-7.53 (4H, m).

EXAMPLE 7

·A solution of 4-oxo-3-thiazolidinylacetyl chloride (1.75 g) in tetrahydrofuran (5.00 ml) was added dropsise to a suspension of 3-(4-piperidyl)indole (2.00 g) and triethylamine (4.10 ml) in a mixture of tetrahydrofuran (15.0 ml) and chloroform (5.00 ml) at 4° to 7° C. with stirring. After the mixture was allowed to stir for 1 hour with ice-bath cooling, the resultant precipitate was removed by filtration and the solvent was evaporated in vacuo. The residue was mixed with saturated aqueous sodium hydrogen carbonate (10.0 ml) and the mixture was extracted with chloroform (20.0 ml). The extract was washed with water, dried over magnesium sulfate and evaporated in vacuo. The residue was recrystallized from a mixture of methanol and acetone to give 4-(3-indolyl)-1-[(4-oxo-3-thiazolidinyl)acetyl]piperidine (0.92 g) as slightly brown prisms.

mp: 174° to 175° C.

IR (Nujol): 3175, 1645, 1625 cm$^{-1}$.

NMR (DMSO-d$_6$, δ): 1.37-2.20 (4H, m), 2.73-4.03 (5H, m), 3.58 (2H, t, J=1 Hz), 4.28 (2H, s), 4.48 (2H, t, J=1 Hz), 6.87-7.70 (5H, m) and 10.87 (1H, br s).

EXAMPLE 8

Thionyl chloride (1.82 ml) was added dropwise to a solution of 4-oxo-3-thiazolidinylacetic acid (1.45 g) in a mixture of dichloromethane (18.2 ml) and tetrahydrofuran (5.00 ml) at room temperature. After the mixture was stirred for 5 hours, the solvent was evaporated in vacuo to give brown semisolid. A solution of the semisolid in tetrahydrofuran (5.00 ml) was added dropwise to a mixture of 1-(4-fluorophenylsulfonyl)piperazine (2.00 g) and triethylamine (2.49 ml) in tetrahydrofuran (10.0 ml) at 0° C. with stirring. The mixture was allowed to stir at that temperature further 1 hour. After the solvent was evaporated in vacuo, the residue was mixed with ethyl acetate (15.0 ml) and water (15.0 ml). The resultant insoluble product was collected by filtration and recrystallized from a mixture of acetone and methanol to give 1-(4-oxo-3-thiazolidinyl)acetyl-4-(4-fluorophenylsulfonyl)piperazine as slightly brown needles.

mp: 201° to 202° C.

IR (Nujol): 1680 (shoulder), 1665, 1350, 1170, 1155 cm$^{-1}$.

NMR (DMSO-d$_6$, δ): 2.83-3.14 (4H, m), 3.43-3.69 (6H, m), 4.18 (2H, s), 4.35 (2H, s) and 7.30-7.93 (4H, m).

EXAMPLE 9

The following compounds were prepared in a similar manner to that of Example 8.

(1) 1-(4-Oxo-3-thiazolidinyl)acetyl-4-benzoylpiperidine (recrystallized from a mixture of ethyl acetate and n-hexane)

mp: 142° to 143° C.

IR (Nujol): 1670, 1655 (shoulder), 1645 cm$^{-1}$.

NMR (CDCl$_3$, δ): 1.57-2.17 (4H, m), 2.73-4.47 (5H, m), 3.62 (2H, t, J=1 Hz), 4.25 (2H, d, J=2 Hz), 4.58 (2H, t, J=1 Hz) and 7.32-8.07 (5H, m).

(2) 1-(4-Oxo-3-thiazolidinyl)acetyl-4-(2-fluorophenylthio)piperidine (recrystallized from a mixture of ethyl acetate and n-hexane)

mp: 99° to 100° C.

IR (Nujol): 1670, 1645 cm$^{-1}$.

NMR (DMSO-d$_6$, δ): 1.03-2.17 (4H, m), 2.67-4.08 (4H, m), 3.52 (2H, t, J=1 Hz), 4.20 (2H, s), 4.40 (2H, t, J=1 Hz) and 7.03-7.67 (4H, m).

(3) 1-(4-Oxo-3-thiazolidinyl)acetyl-4-(2-fluorophenylsulfonyl)piperidine (recrystallized from ethanol)

mp: 150° to 151° C.

IR (Nujol): 1680, 1660, 1325, 1150 cm$^{-1}$.

NMR (DHSD-d$_6$, δ): 1.07-2.13 (4H, m), 2.67-4.10 (5H, m), 3.53 (2H, t, J=1 Hz), 4.22 (2H, s), 4.40 (2H, t, J=1 Hz) and 7.33-8.05 (4H, m).

(4) 3-(4-Oxo-3-thiazolidinylacetyl)thiazolidine (recrystallized from a mixture of ethyl acetate and n-hexane)

mp: 106° to 107° L C.

IR (Nujol): 1675, 1650 cm$^{-1}$.

NMR (DMSO-d$_6$, δ): 3.12 (2H, t, J=7 Hz), 3.55 (2H, t, J=1.5 Hz), 3.73 (2H, t, J=7 Hz), 4.23 (2H, s), 4.43 (2H, t, J=1.5 Hz) and 4.48-4.65 (2H, m).

(5) N-Phenyl-4-oxo-3-thiazolidinylacetamide (recrystallized from a mixture of acetone and methanol)

mp: 218° to 219° C.

IR (Nujol): 1680 (shoulder), 1660 cm$^{-1}$.

NMR (DMSO-d$_6$, δ): 3.55 (2H, t, J=1 Hz), 4.15 (2H, s), 4.50 (2H, t, J=1 Hz), 6.87-7.63 (5H, m) and 10.05 (1H, br s).

(6) N-(3-Pyridyl)-4-oxo-3-thiazolidinylacetamide (recrystallized from a mixture of methanol and N,N-dimethylformamide)

mp: 205° to 206° C.

IR (Nujol): 3310, 3275, 3180, 3125, 3075, 1690, 1650 cm$^{-1}$.

NMR (DMSO-d$_6$, δ): 3.60 (2H, t, J=1.5 Hz), 4.23 (2H, s), 4.57 (2H, t, J=1.5 Hz), 7.36 (1H, dd, J=8 Hz and 4 Hz), 8.03 (1H, d, t, J=8 Hz and 2 Hz), 8.30 (1H, d, J=2 Hz), 8.77 (1H, d, J=2 Hz) and 10.33 (1H, s).

(7) N-Benzyl-4-oxo-3-thiazolidinylacetamide (recrystallized from a mixture of ethanol and ethyl acetate).
mp: 139° to 140° C.
IR (Nujol): 1660, 1645 cm$^{-1}$.
NMR (DMSO-d$_6$, δ): 3.58 (2H, t, J=1.5 Hz, 4.06 (2H, s), 4.34 (2H, d, J=6 Hz), 4.51 (2H, t, J=1.5 Hz), 7.33 (5H, s) and 8.50 (1H, t, J=6 Hz).
(8) N-Furfuryl-4-oxo-3-thiazolidinylacetamide (recrystallized from ethyl acetate)
mp: 124° to 125° C.
IR (Nujol): 1650 cm$^{-1}$.
NMR (DMSO-d$_6$, δ): 3.48 (2H, t, J=1.5 Hz), 3.93 (2H, s), 4.25 (2H, d, J=5.5 Hz), 4.42 (2H, t, J=1.5 Hz), 6.15–6.38 (2H, m), 7.45–7.53 (1H, m) and 8.43 (1H, t, J=5.5 Hz).

EXAMPLE 10

The following compounds were prepared in a similar manner to that of Example 1.
(1) Monooxalic acid salt of 1-(4-oxo-3-thiazolidinyl)acetyl-4-[α-(4-chlorophenyl)benzyl]piperazine (recrystallized from a mixture of acetone and diethylether)
mp: 117° to 126° C.
IR (Nujol): 1720, 1660 cm$^{-1}$.
NMR (DMSO-d$_6$, δ): 2.18–2.40 (4H, m), 3.32–3.63 (4H, m), 3.52 (2H, s), 4.17 (2H, s), 4.38 (2H, s), 4.43 (1H, s), 7.22–7.60 (9H, m) and 9.25 (2H, br s).
(2) Monohydrochloric acid salt of 1-(4-oxo-3-thiazolidinyl)acetyl-4-(2-hydroxy)ethylpiperazine (recrystallized from a mixture of ethanol and diethyl ether)
mp: >128° C.
IR (Nujol): 3460, 1650 (shoulder), 1630 cm$^{-1}$.
NMR (DMSO-d$_6$, δ): 2.83–4.07 (8H, m), 3.18 (2H, t, J=5 Hz), 5.30 (2H, s), 3.82 (2H, t, J=5 Hz), 4.30 (2H, s), 4.39 (2H, s) and 11.17 (1H, br s).
(3) 4-(4-Oxo-3-thiazolidinyl)acetylmorpholine (recrystallized from methanol)
mp: 155° and 156° C.
IR (Nujol): 1680 (shoulder), 1650 (shoulder), 1635 cm$^{-1}$.
NMR (DMSO-d$_6$, δ): 3.30–3.70 (10H, m), 2.22 (2H, s), and 4.42 (2H, t, J=1.5 Hz).
(4) Monosulfuric acid salt of 1-(4-oxo-3-thiazolidinyl)acetyl-4-diphenylmethylhomopiperazine (recrystallized from ethanol)
mp: 198° to 199° C.
IR (Nujol): 1665, 1645 cm$^{-1}$.
NMR (DMSO-d$_6$, δ): 1.83–2.20 (2H, m), 2.97–3.97 (8H, m), 3.52 (2H, s), 4.23 (2H, s), 4.42 (2H, s), 5.70 (1H, s) and 7.17–7.83 (10H, m).

EXAMPLE 11

The following compounds were prepared in a similar manner to that of Example 5.
(1) 3-Benzoyl-4-oxothiazolidine (recrystallized from ethyl acetate)
mp: 139° to 140° C.
IR (Nujol): 1735, 1660 cm$^{-1}$.
NMR (DMSO-d$_6$, δ): 3.75 (2H, s), 4.88 (2H, s) and 7.23–7.73 (5H, m).
Anal. calcd for C$_{10}$H$_9$NO$_2$S: C; 57.95, H; 4.38, N; 6.76. Found: C; 58.25, H; 4.26, N; 6.69.
(2) 3-(4-Methylbenzoyl)-4-oxothiazolidine (recrystallized from a mixture of ethyl acetate and n-hexane)
mp: 122° to 123° C.
IR (Nujol): 1725, 1665 cm$^{-1}$.
NMR (CDCl$_3$, δ): 2.40 (3H, s), 3.63 (2H, s), 4.85 (2H, s), 7.16 (1H, d, J=9 Hz) and 7.50 (1H, d, J=9 Hz).
(3) 3-(4-Chlorobenzoyl)-4-oxothiazolidine (recrystallized from a mixture of ethyl acetate and n-hexane)
mp: 116° to 117° C.
IR (Nujol): 1710, 1670 cm$^{-1}$.
NMR (CDCl$_3$, δ): 3.67 (2H, s), 4.88 (2H, s), 7.33 (2H, d, J=8 Hz) and 7.55 (2H, d, J=8 Hz).
(4) 3-(4-Trifluoromethylbenzoyl)-4-oxothiazolidine (recrystallized from ethanol)
mp: 102° to 104° C.
IR (Nujol): 1750, 1685 cm$^{-1}$.
NMR (CDCl$_3$, δ): 3.67 (2H, s), 4.90 (2H, s) and 7.65 (4H, s).
(5) 3-(2,4-Dimethoxybenzoyl)-4-oxothiazolidine (recrystallized from a mixture of acetone and methanol)
mp: 147° to 149° C.
IR (Nujol): 1715, 1680 cm$^{-1}$.
NMR (DMSO-d$_6$, δ): 3.72 (2H, s), 3.73 (3H, s), 3.78 (3H, s), 4.82 (2H, s), 6.50 (1H, dd, J=9 Hz and 2 Hz), 6.52 (1H, d, J=2 Hz) and 7.20 (1H, d, J=9 Hz).
(6) 3-(3-Pyridinecarbonyl)-4-oxothiazolidine (recrystallized from ethanol)
mp: 81° to 82° C.
IR (Nujol): 1745, 1670 cm$^{-1}$.
NMR (CDCl$_3$, δ): 3.73 (2H, s), 4.97 (2H, s), 7.27–7.47 (1H, m), 7.77–8.00 (1H, m) and 8.70–8.83 (2H, m).
(7) 3-(2-Furoyl)-4-oxothiazolidine (recrystallized from a mixture of ethyl acetate and n-hexane)
mp: 101° to 102° C.
IR (Nujol): 1715, 1675 cm$^{-1}$.
NMR (CDCl$_3$, δ): 3.70 (2H, s), 4.85 (2H, s), 6.53 (1H, dd, J=4 Hz and 2 Hz), 7.29 (1H, d, J=4 Hz) and 7.59 (1H, d, J=2 Hz).
(8) 3-(2-Thenoyl)-4-oxothiazolidine (recrystallized from a mixture of ethyl acetate and diisopropyl ether)
mp: 86° to 87° C.
IR (Nujol): 1715, 1650 cm$^{-1}$.
NMR (CDCl$_3$, δ): 3.70 (2H, s), 4.87 (2H, s), 7.00–7.23 (1H, m) and 7.52–7.80 (2H, m).

EXAMPLE 12

Sodium hydride (60% dispersion in mineral oil) (0.58 g) was added portionwise to a solution of 4-oxothiazolidine (1.50 g) and 4-methoxybenzenesulfonyl chloride (3.01 g) in tetrahydrofuran (30 ml) at 0° C. with stirring and the mixture was stirred for 1 hour at the same temperature. After the solvent was evaporated in vacuo, the residue was mixed with ethyl acetate (10 ml) and water (50 ml) and the resultant precipitate was collected by filtration. The cake was washed with water and diisopropyl ether and recrystallized from a mixture of ethanol and ethyl acetate to give 3-(4-methoxybenzenesulfonyl)-4-oxothiazolidine (1.65 g) as slightly brown prisms.
mp: 129° to 130° C.
IR (Nujol): 1710, 1365, 1155 cm$^{-1}$.
NMR (DMSO-d$_6$, δ): 3.65 (2H, s), 3.87 (3H, s), 4.92 (2H, s), 7.62 (2H, d, J=9 Hz) and 7.96 (2H, d, J=9 Hz).

EXAMPLE 13

A solution of m-chloroperbenzoic acid (0.84 g) in dichloromethane (15 ml) was added dropwise to a solution of 1-(4-oxo-3-thiazolidinyl)acetyl-4-diphenylmethylpiperazine (1.45 g) in dichloromethane (15 ml) at 0° C. with stirring. After the solution was allowed to stir for 2 hours at the same temperature, mixed with saturated aqueous sodium hydrogen carbonate (30 ml). The organic layer was separated, washed with water and dried over magnesium sulfate. The evaporated residue was recrystallized from a mixture of acetone and methanol to give 4-oxo-3-(4-diphenylmethylpiperazin-1-ylcarbonylmethyl)thiazolidine-1-oxide as colourless prisms.

mp: 225° to 226° C.

IR (Nujol): 1680, 1650, 1610 cm$^{-1}$.

NMR (CDCl$_3$—CD$_3$OD, δ): 2.23–2.63 (4H, m), 3.27–3.70 (6H, m), 3.80–4.95 (5H, m) and 7.10–7.53 (10H, m).

EXAMPLE 14

(Preparation of granules or small granules)

| | |
|---|---|
| 1-(4-Oxo-3-thiazolidinyl)acetyl-4-diphenylmethylpiperazine | 500 (g) |
| Sucrose | 9250 |
| Hydroxypropylcellulose | 200 |
| Starch | 50 |

The above ingredients are blended and granulated or grained in a conventional manner into granules or small granules.

EXAMPLE 15

A solution of potassium permanganate (0.34 g) in water (3.5 ml) was added dropwise to a solution of 1-(4-oxo-3-thiazolidinyl)acetyl-4-diphenyl-methylpiperazine (0.5 g) in acetic acid (5 ml) with stirring over a period of 5 minutes at 20° C. and the mixture was stirred at ambient temperature for 1 hour. The resultant mixture was washed with aqueous sodium bisulfite and was extracted with chloroform (10 ml). The aqueous layer was extracted with chloroform. The combined chloroform layer was washed with water, dried over magnesium sulfate and filtered. The fltrate was evaporated in vacuo to give a solid (0.42 g). The solid was dissolved in chloroform and subjected to a column chromatography using chloroform as an eluent. The fraction containing the object compound was evaporated in vacuo to give 4-oxo-3-(4-diphenylmethylpiperazin-1-ylcarbonylmethyl)thiazolidine-1,1-dioxide (0.15 g) as a colourless prisms.

mp: 209° to 211° C.

IR (Nujol): 1675, 1640, 1420 cm$^{-1}$.

NMR (CDCl$_3$, δ): 2.17–2.55 (4H, m), 3.2–3.7 (4H, m), 3.78 (2H, s), 4.25 (3H, s), 4.65 (2H, s), 6.95–7.55 (10H, m).

EXAMPLE 16

A solution of m-chloroperbenzoic acid (0.87 g) in dichloromethane (10 ml) was added dropwise to a solution of 1-(4-oxo-3-thiazolidinyl)acetyl-4-diphenylmethylpiperazine (1 g) in dichloromethane (10 ml) with stirring over a period of 30 minutes at 10° C. and the mixture was stirred for 5.5 hours at ambient temperature. To the resultant mixture was added N,N-dimethylformamide (20 ml) and then the mixture was stirred overnight at the same temperature. To the resultant mixture was added in ice water (100 ml), chloroform (100 ml) and aqueous sodium iodide. The chloroform layer was washed with aqueous sodium thiosulfate and brine, dried over magnesium sulfate and filtered. the filtrate was evaporated in vacuo to give an oily residue. The residue was pulverized with ether and diisopropylether to give precipitate. The precipitate was washed with diisopropyl ether and dried to give 4-oxo-3-(4-diphenylmethylpiperazin-1-yl-carbonylmethyl)thiazolidine-S,N$^4$-dioxide represented by the formula:

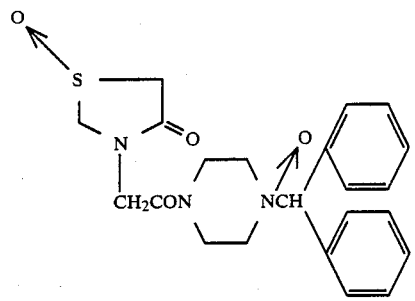

mp: 161.5°–164° C.

IR(Nujol): 1690, 1675, 1640, 1490, 1480, 1415 cm$^{-1}$.

NMR (CDCl$_3$, δ): 2.45–3.7 (10H, m), 3.75 (1H, d, J=17 Hz), 4.22 (1H, d, J=12 Hz), 4.68 (1H, d, J=17 Hz), 4.85 (1H, d, J=12 Hz), 5.68 (1H, s), 7.1–7.4(10H, m).

MASS (M/Z): 427 (M+).

EXAMPLE 17

To 1-(4-oxo-3-thiazolidinyl)acetyl-4-diphenylmethylpiperazine (1.00 g) was added water (1.5 ml) and 1N hydrochloric acid (3.5 ml). The mixture was vigorously stirred for 10 minutes, allowed to stand for 10 minutes at 50° C. and stirred for 30 minutes at 50° C. and for 24 hours at ambient temperature to precipitate crystals. The crystals was obtained by filtration and dried under reduced pressure to give monohydrochloric acid salt of 1-(4-oxo-3-thiazolidinyl)acetyl-4-diphenylmethylpiperazine (0.9 g).

mp: 220°–222° C. (dec.).

IR (Nujol): 1680(s), 1660 cm$^{-1}$.

The following salts were obtained in a similar manner to that of the above.

(1) ½ Sulfuric acid salt of 1-(4-oxo-3-thiazolidinyl)-acetyl-4-diphenylmethylpiperazine IR (Nujol): 1650 cm$^{-1}$.

(2) Monohydrobromic acid salt of 1-(4-oxo-3-thiazolidinyl)acetyl-4-diphenylmethyl-piperazine IR (Nujol); 1650 cm$^{-1}$.

We claim:

1. Oxothiazolidine compound of the formula:

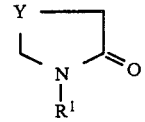

wherein

R$^1$ is benzoyl which may have one or two substituent(s) selected from lower alkyl, lower alkoxy, halogen and trihalomethyl;
benzenesulfonyl which may have lower alkoxy;
pyridylcarbonyl;
furoyl;
thenoyl;
di(lower)alkylamino-(lower)alkylcarbamoyl-(lower)alkyl;
phenylcarbamoyl(lower) alkyl;
xylylcarbamoyl(lower)alkyl;
phenyl(lower)alkyl-carbamoyl(lower)alkyl;
pyridylcarbamoyl(lower) alkyl;

furyl(lower)alkylcarbamoyl-(lower)alkyl; thiazolidinylcarbonyl(lower)alkyl; morpholinylcarbonyl(lower)alkyl or a group of the formula:

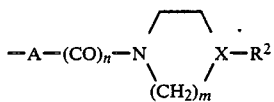

in which
A is lower alkylene;
n is an integer of 1;
m is an integer of 2 or 3;
x is —N—,

or —CH— and
$R^2$ is hydroxy;
lower alkyl which may have hydroxy;
mono(or di)phenyl(lower)alkyl which may have halogen;
phenylthio which may have halogen;
benzoyl;
benzenesulfonyl which may have halogen; or
indolyl and Y is —S—,

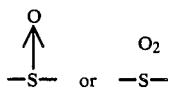

or pharmaceutically acceptable salts thereof.

2. The compound of claim 1, which is a compound of the formula:

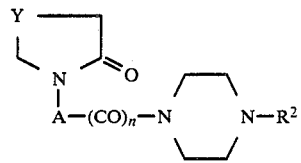

wherein A, n, $R^2$ and Y are each as defined in claim 1 or pharmaceutically acceptable salt thereof.

3. The compound of claim 2, wherein
A and Y are each as defined in claim 1,
n is 1 and
$R^2$ is ar(lower)alkyl which may have halogen.

4. The compound of claim 3, which is 1-(4-oxo-3-thiazolidinyl)acetyl-4-diphenylmethylpiperazine or pharmaceutically acceptable salt thereof.

5. The compound of claim 3, which is 4-oxo-3-(4-diphenylmethylpiperazin-1-ylcarbonylmethyl)thiazolidine-1-oxide or pharmaceutically acceptable salt thereof.

6. The compound of claim 3 which is 4-oxo-3-(4-diphenylmethylpiperazin-1-yl-carbonylmethyl)thiazolidine-1,1-dioxide.

7. The compound of claim 1 wherein Y is as defined in claim 1 and $R^1$ is benzoyl which may have one or two substituent(s) selected from lower alkyl, lower alkoxy, halogen and trihalomethyl; benzonesulfonyl which may have lower alkoxy; pyridylcarbonyl; furoyl; thenoyl.

8. The compound of claim 7, which is 3-(4-methoxybenzoyl)-4-oxothiazolidine or pharmaceutically acceptable salt thereof.

9. A pharmaceutical composition useful in treating patients suffering from senility, lost or impaired memory, or amnesia comprising, an effective amount of one or more oxothiazolidine compound of claim 1 or pharmaceutically acceptable salt thereof and pharmaceutically accepted carrier.

* * * * *